(12) United States Patent
Nakagawa

(10) Patent No.: US 11,213,306 B2
(45) Date of Patent: Jan. 4, 2022

(54) CATHETER

(71) Applicant: ASAHI INTECC CO., LTD., Seto (JP)

(72) Inventor: Yuta Nakagawa, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 145 days.

(21) Appl. No.: 16/657,250

(22) Filed: Oct. 18, 2019

(65) Prior Publication Data

US 2020/0121332 A1 Apr. 23, 2020

(30) Foreign Application Priority Data

Oct. 19, 2018 (JP) .............................. JP2018-197339

(51) Int. Cl.
*A61B 17/22* (2006.01)
*A61F 2/01* (2006.01)
*A61M 25/00* (2006.01)

(52) U.S. Cl.
CPC .......... *A61B 17/22* (2013.01); *A61M 25/0023* (2013.01); *A61B 2017/22042* (2013.01);
(Continued)

(58) Field of Classification Search
CPC .................. A61B 17/22; A61B 17/221; A61B 17/320725; A61B 2017/22042; A61B 2017/22094; A61B 2017/22001; A61B 2017/2215; A61M 25/0023; A61M 25/04; A61F 2/01; A61F 2/013; A61F 2/90
See application file for complete search history.

(56) References Cited

U.S. PATENT DOCUMENTS

| 4,771,778 A * | 9/1988 | Mar ................. A61M 25/09033 |
| | | 604/103.1 |
| 2017/0105742 A1* | 4/2017 | Nishigishi ............ A61B 17/221 |

(Continued)

FOREIGN PATENT DOCUMENTS

| EP | 3158954 A1 | 4/2017 |
| JP | 3655920 B2 | 6/2005 |

(Continued)

OTHER PUBLICATIONS

Apr. 15, 2020 Extended Search Report issued in European Patent Application No. 19203835.4.
(Continued)

*Primary Examiner* — Tuan V Nguyen
(74) *Attorney, Agent, or Firm* — Oliff PLC

(57) ABSTRACT

A catheter includes a first hollow shaft made of a first material, a second hollow shaft made of a second material, a mesh member with a tubular shape configured to expand and contract in a radial direction, a front end tip, and a core wire. The core wire extends inside the mesh member, inside a lumen of the second hollow shaft, and inside a lumen of the first hollow shaft. The core wire has a front end side small-diameter portion and a large-diameter portion. The large-diameter portion has an outer diameter larger than an outer diameter of the front end side small-diameter portion, and is located on the base end side relative to the front end side small-diameter portion. At least a portion of the large-diameter portion is located in the lumen of the second hollow shaft in a state where the mesh member remains contracted radially.

6 Claims, 10 Drawing Sheets

(52) U.S. Cl.
CPC .............. *A61B 2017/22065* (2013.01); *A61B 2017/22094* (2013.01); *A61F 2/011* (2020.05); *A61F 2002/016* (2013.01)

(56) References Cited

U.S. PATENT DOCUMENTS

| | | |
|---|---|---|
| 2020/0046388 A1 | 2/2020 | Ogidou et al. |
| 2020/0046937 A1 | 2/2020 | Nakagawa et al. |

FOREIGN PATENT DOCUMENTS

| | | |
|---|---|---|
| WO | 9424946 A1 | 11/1994 |
| WO | 2018193600 A1 | 10/2018 |
| WO | 2018193601 A1 | 10/2018 |

OTHER PUBLICATIONS

Shinsuke Nanto, Ed. Yodosha Co., Ltd., "Kakuzitsuni Minitsuku Pci No Kihon To Kotsu", Revised edition, pp. 222-227, Feb. 25, 2016.

* cited by examiner

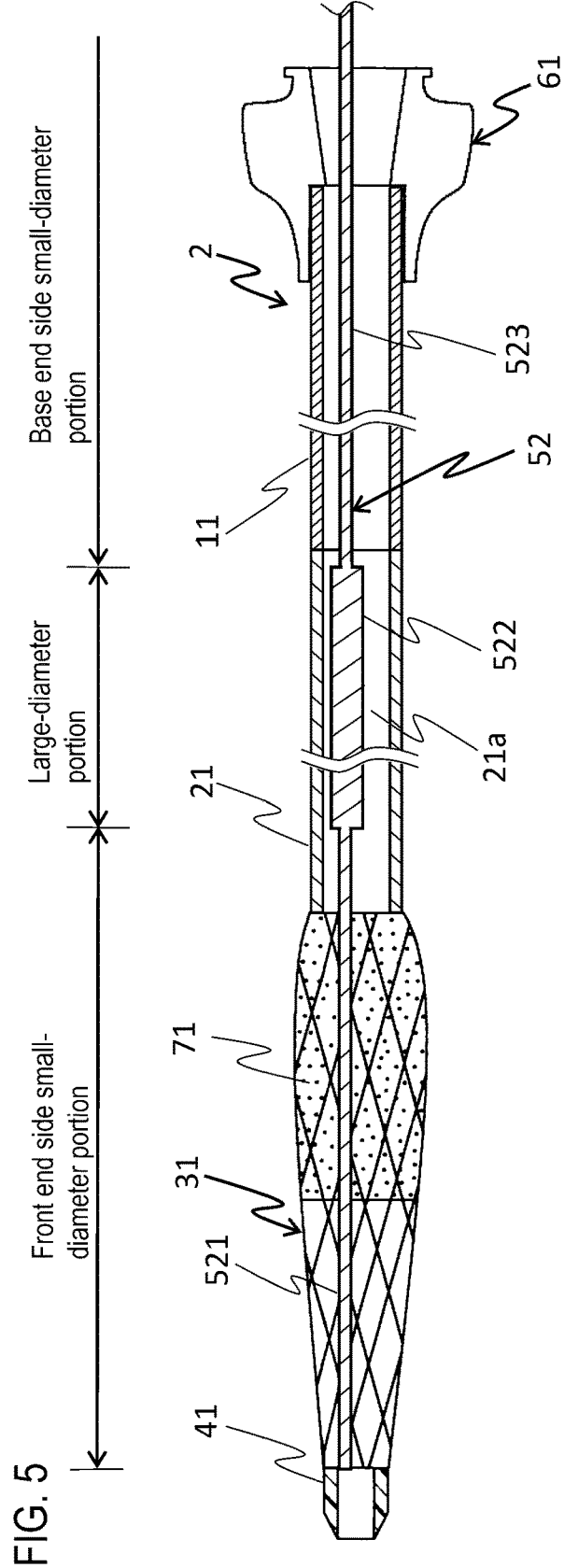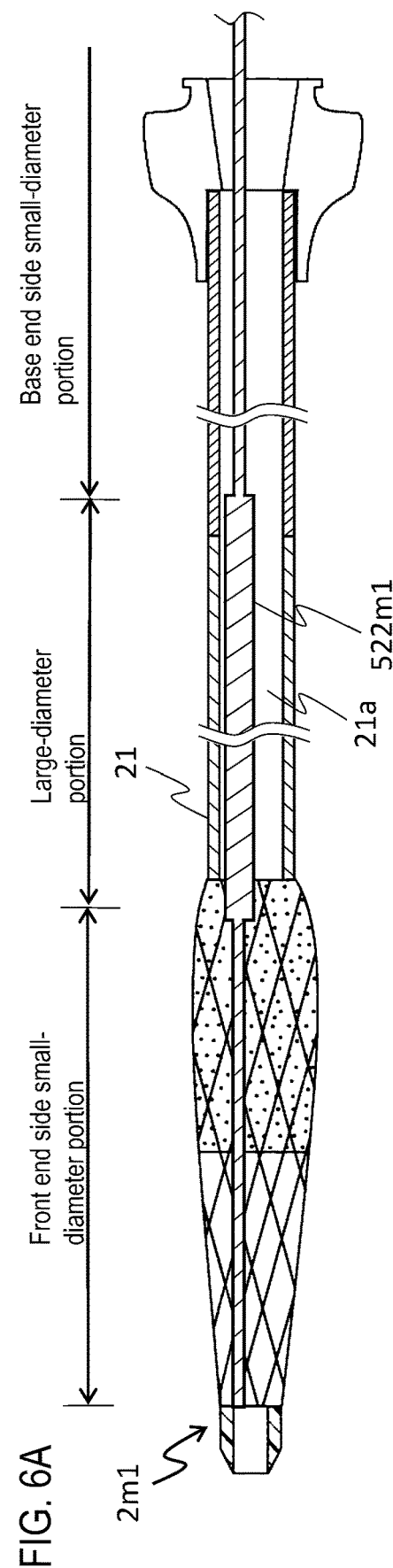

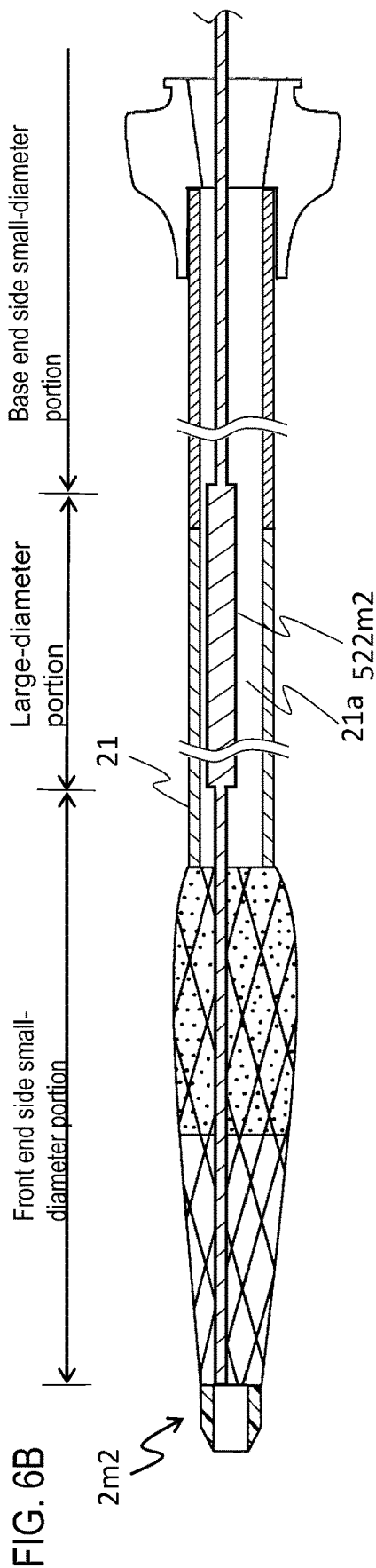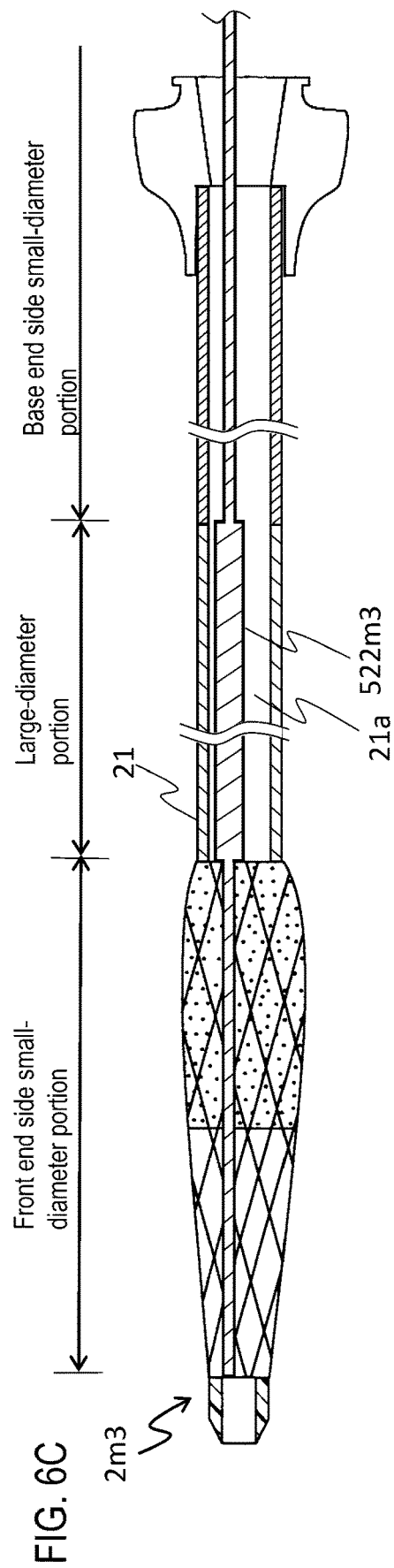

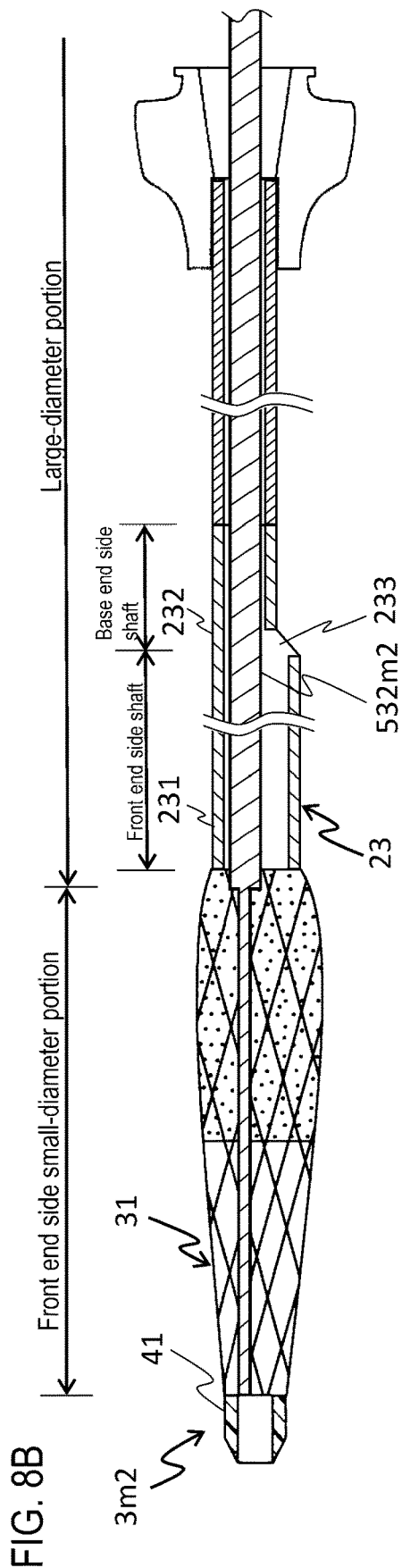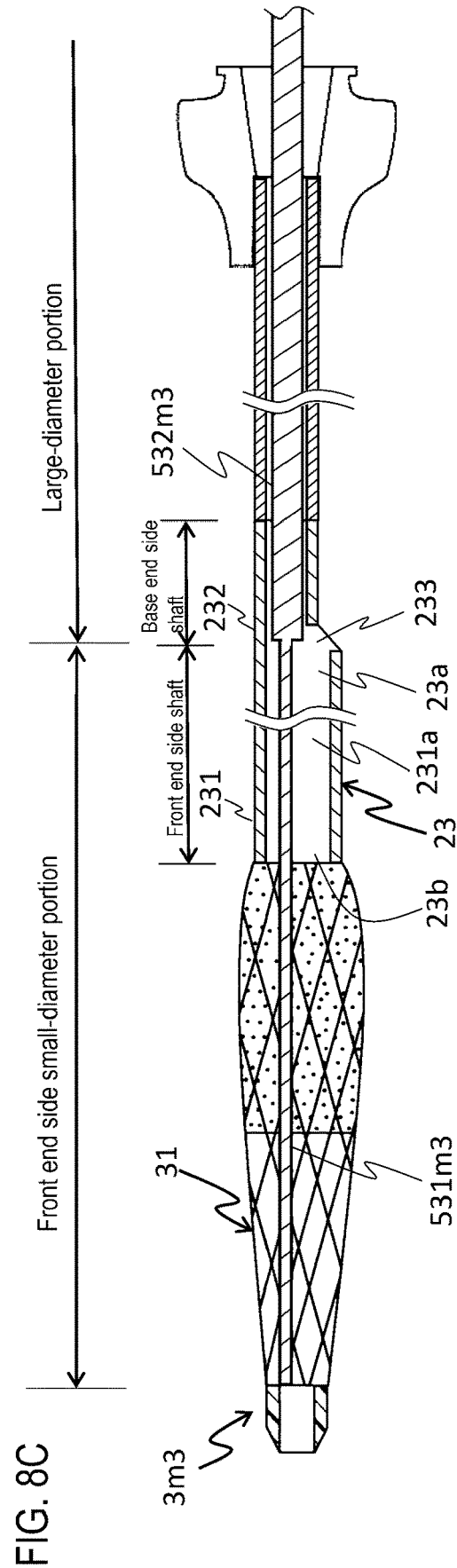
FIG. 8B
FIG. 8C

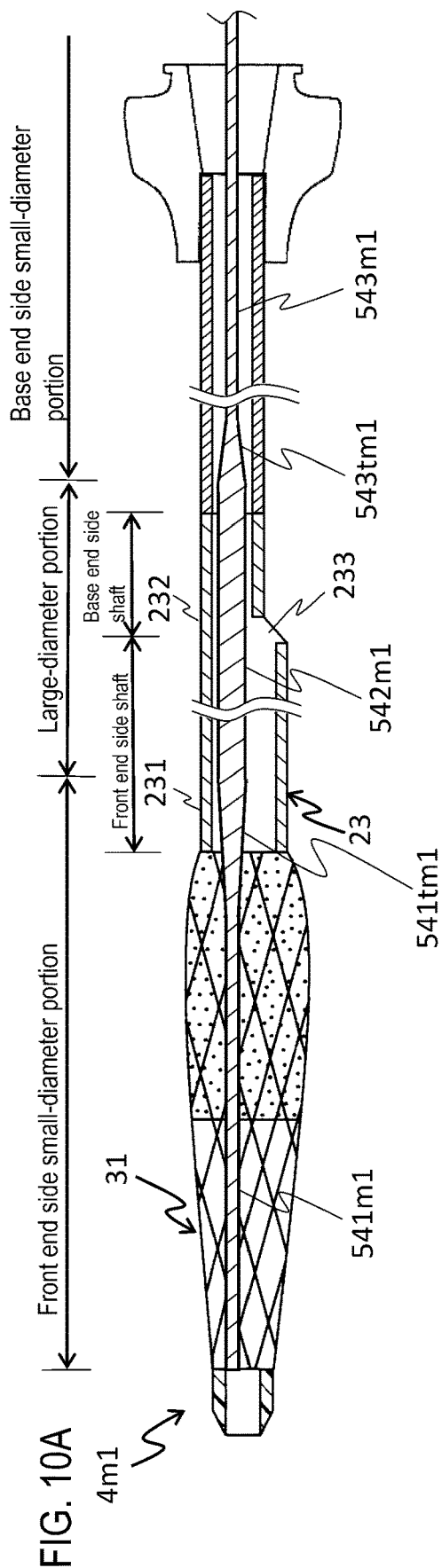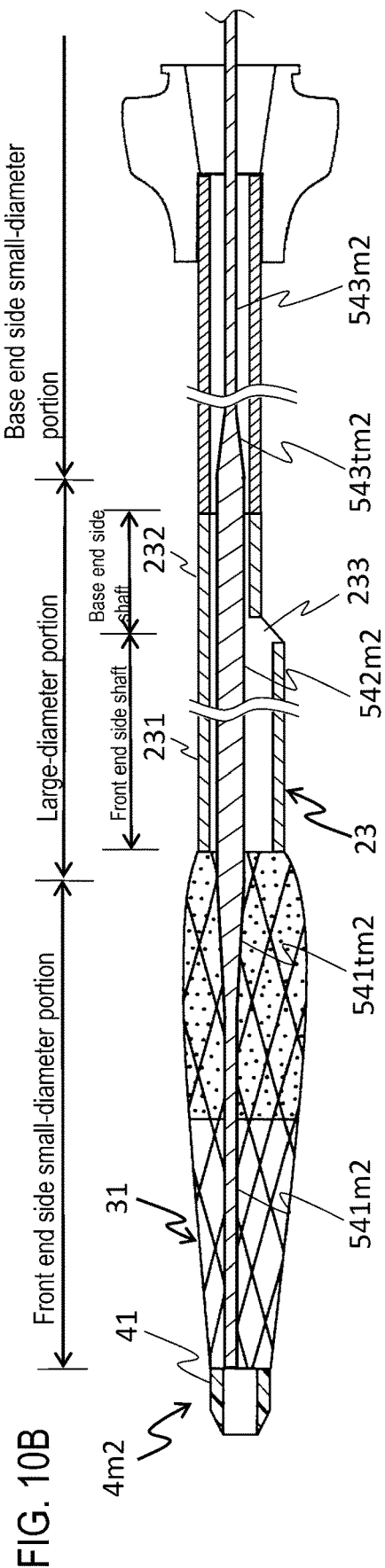

CATHETER

CROSS REFERENCE TO RELATED APPLICATION

This application claims priority from Japanese Patent Application No. 2018-197339 filed Oct. 19, 2018. The entire content of the priority application is incorporated herein by reference.

TECHNICAL FIELD

The present invention relates to a medical device, and specifically to a catheter.

BACKGROUND

As a medical device for removing a blood vessel-occluding blockage such as chronic total occlusion (CTO) to improve a blood flow, for example, a technology is disclosed involving expanding a false lumen using an antegrade guide wire, and then passing a retrograde guide wire through the false lumen, according to a document (Shinsuke Nanto, Ed. "Kakuzitsuni minitsuku PCI no kihon to kotsu, Revised edition," Yodosha Co., Ltd., Feb. 25, 2016, pp. 222-227).

The above technology is called the Reverse CART method in which, for example, a catheter having a mesh-like member in the side of an antegrade guide wire is placed inside a blood vessel so that a retrograde guide wire can be captured through a mesh opening formed after expansion of the above member.

SUMMARY

The conventional catheter as described above has a body formed of a soft resin so as to be able to freely advance or retract through a curved blood vessel. This, however, may sometimes cause excessive bending of the catheter body, resulting in a kink.

The present disclosure is made in view of the above circumstances. An object of the present disclosure is to provide a catheter capable of preventing the occurrence of a kink in a resin hollow shaft.

To achieve the above object, a catheter according to an embodiment of the present disclosure includes: a first hollow shaft made of a first material, a second hollow shaft made of a second material and connected to a front end of the first hollow shaft, a mesh member with a tubular shape, the mesh member being connected to a front end of the second hollow shaft and capable of expanding and contracting in a radial direction, a front end tip connected to a front end of the mesh member, and a core wire having a front end connected to the front end of the mesh member and/or connected to the front end tip, the core wire extending through an inside of the mesh member and lumens of the second hollow shaft and the first hollow shaft so that a base end of the core wire is located on a base end side relative to a base end of the first hollow shaft, wherein the core wire has a front end side small-diameter portion, and a large-diameter portion having an outer diameter larger than the outer diameter of the front end side small-diameter portion and located on the base end side relative to the front end side small-diameter portion, and at least a portion of the large-diameter portion is located in the lumen of the second hollow shaft in a state where the mesh member remains radially contracted.

It is noted that the term "front end side" as used herein means a direction along the long axis direction of the first and second hollow shafts, in which the mesh member is located relative to the second hollow shaft. Further, the term "base end side" as used herein means a direction along the long axis direction of the first and second hollow shafts, and opposite to the front end side. Moreover, the term "front end" refers to an end of any member or portion in the front end side while the term "base end" refers to an end of any member or portion in the base end side.

BRIEF DESCRIPTION OF THE DRAWINGS

FIG. 5 shows a schematic cross-sectional view of a second embodiment.

FIGS. 6A, 6B, and 6C show schematic cross-sectional views of variations of the second embodiment.

FIGS. 8A, 8B, and 8C show schematic cross-sectional views of variations of the core wire of the third embodiment.

FIGS. 10A, 10B, 10C and 10D show schematic cross-sectional views of variations of the core wire of the fourth embodiment.

DETAILED DESCRIPTION

A catheter according to an embodiment of the present disclosure includes: a first hollow shaft made of a first material, a second hollow shaft made of a second material, for example, less rigid than the first material, and connected to a front end of the first hollow shaft, a mesh member with a tubular shape connected to a front end of the second hollow shaft and configured to expand and contract in a radial direction, a front end tip connected to a front end of the mesh member, and a core wire having a front end connected to the front end of the mesh member and/or the front end tip, and extending inside the mesh member, inside a lumen of the second hollow shaft, and inside a lumen of the first hollow shaft so that a base end is located on a base end side of the catheter relative to a base end of the first hollow shaft, wherein the core wire has a front end side small-diameter portion, and a large-diameter portion having a diameter larger than the outer diameter of the front end side small-diameter portion and located in the base end side relative to the front end side small-diameter portion, and at least a portion of the large-diameter portion is located in the lumen of the second hollow shaft in a state where the mesh member remains radially contracted.

It is noted that the term "antegrade guide wire" means a guide wire used for directing the present catheter through a body cavity such as a blood vessel while the term "retrograde guide wire" means a guide wire which is used so as to approach the present catheter from the opposite direction through the body cavity.

Below, the first to fourth embodiments will be described with reference to the drawings, but the present disclosure shall not only be limited the embodiments shown in the present drawings. Further, the dimensions of catheters shown in the figures are merely provided to facilitate understanding of the embodiments, but do not necessarily correspond to the actual dimensions.

First Embodiment

Figure 1:
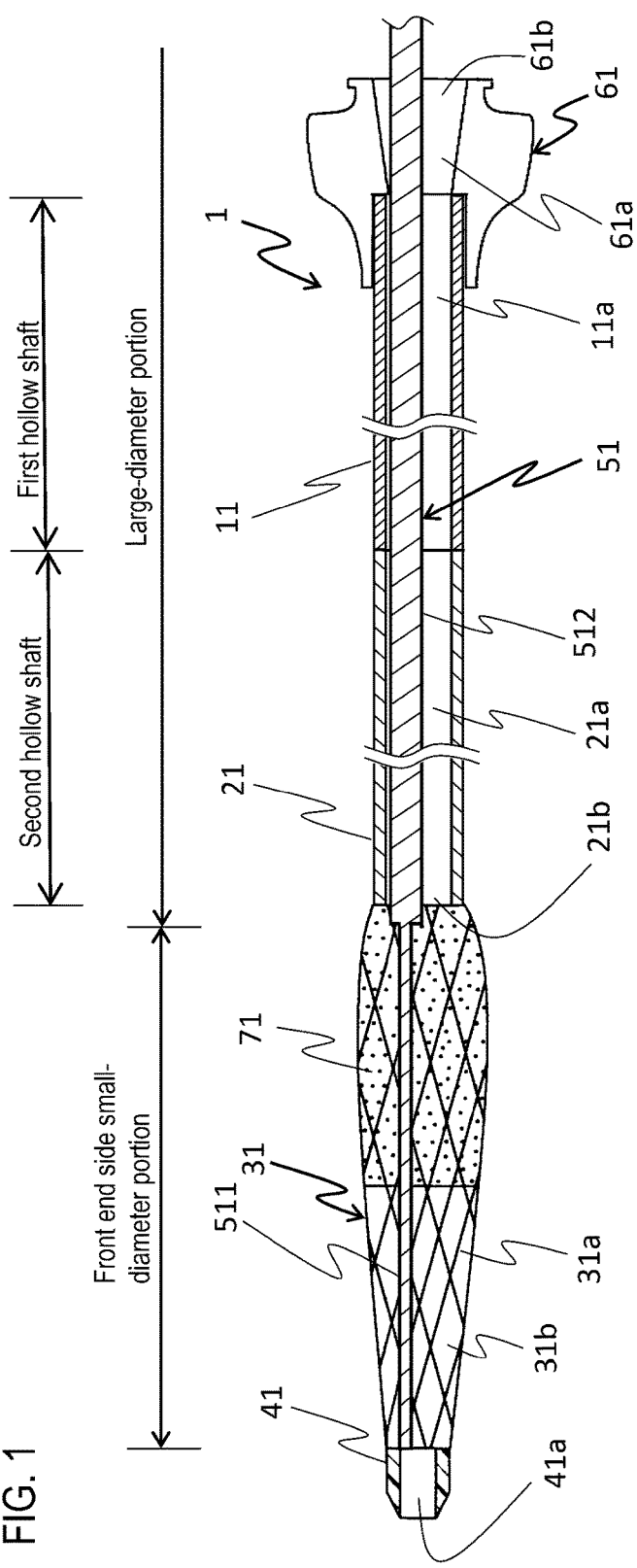
FIG. 1 shows a schematic cross-sectional view of a first embodiment.

FIG. 1 shows a schematic cross-sectional view of the first embodiment. As shown in FIG. 1, a catheter 1 according to the first embodiment generally includes: a first hollow shaft 11, a second hollow shaft 21, a mesh member 31, a front end tip 41, a core wire 51, a connector 61, and a guiding film 71.

The first hollow shaft 11 is, for example, a metal shaft which is hollow. Specifically, the above first hollow shaft 11, for example, has a lumen 11a extending from a front end through a base end, into which, for example, a core wire 51, a retrograde guide wire W, and the like as described below (see FIG. 3) will be inserted.

A metal material for the first hollow shaft 11 preferably has antithrombogenicity, biocompatibility, and flexibility because the first hollow shaft 11 will be inserted into a body cavity such as a blood vessel. Such metal materials include, for example, stainless steel such as SUS304, nickel-titanium alloy, cobalt-chromium alloy, and the like.

The second hollow shaft 21 is, for example, a resin shaft which is hollow and connected to the front end of the first hollow shaft 11. Specifically, the above second hollow shaft 21 has, for example, a lumen 21a extending from a front end through a base end, and is joined (fixed) to the first hollow shaft 11 so that the lumen 21a is in communication with the lumen 11a of the aforementioned first hollow shaft 11. For example, the core wire 51, the retrograde guide wire W, and the like as described below (see FIG. 3) will be inserted into the lumen 21a.

A resin material for the second hollow shaft 21 preferably has antithrombogenicity, biocompatibility, and flexibility because the second hollow shaft 21 will be inserted into a body cavity such as a blood vessel. The resin material of the second hollow shaft 21 is, for example, less rigid than the metal material of the first hollow shaft 11. Such resin materials include, for example, polyamide resin, polyolefin resin, polyester resin, polyurethane resin, silicone resin, fluororesin, and the like.

As a method of joining the second hollow shaft 21 with the first hollow shaft 11, the following may be used: for example, a method of adhesion involving use of an adhesive, a method involving fusing the second hollow shaft 21 with the first hollow shaft 11 by heating and the like, a method of connection involving use of a connecting member (not shown), and the like.

The mesh member 31 is a tubular member connected to the front end of the second hollow shaft 21, and capable of expanding and contracting in the radial direction. Specifically, the mesh member 31, for example, includes a wire 31a braided in a mesh manner, and can easily be deformed (expanded and contracted) and also can receive the retrograde guide wire W through a mesh opening 31b. The mesh member 31 has a base end portion joined (fixed) to a front end portion of the second hollow shaft 21. Therefore, when the core wire 51 described below is pulled toward the base end side, the mesh member 31 can inflate outwardly in the radial direction to expand radially and enlarge the mesh opening 31b, through which the retrograde guide wire W is allowed to be brought into the inside of the mesh member 31. On the other hand, when the base end portion of the core wire 51 is pushed into the first hollow shaft 11 toward the front end side, the mesh member 31 can contract radially, and become compact. As a result, the present catheter 1 can be easily moved along a body cavity.

Materials for the wire 31a of the mesh member 31 include, for example, metal materials such as stainless steel such as SUS304, nickel titanium alloy, and cobalt-chromium alloy; resin materials such as polyamide, polyester, polyacrylate, and polyetheretherketone; and the like. Among these, metal materials are preferred in view of improving strength and flexibility. It is noted that when the mesh member 31 is composed of a plurality of wires, these wires may be formed of the same material, or may be formed of different materials.

As a method of joining the mesh member 31 with the second hollow shaft 21, the following and the like may be used: for example, a method involving embedding the base end portion of the mesh member 31 into the front end portion of the second hollow shaft 21 by fusion and the like.

The front end tip 41 is connected to the front end of the mesh member 31. For example, the above front end tip 41 can reduce resistance exerted when the catheter 1 advances through the inside of a body cavity, allowing the catheter 1 to advance smoothly. Specifically, the front end tip 41 can be formed so as to have, for example, a lumen 41a for insertion of a guide wire (for example, an antegrade guide wire (not shown)) and a front end portion having a broadly sharp shape which is rounded toward the front end side. The front end tip 41 has a base end portion joined (fixed) to the front end portion of the mesh member 31.

A material for the front end tip 41 preferably has softness so that impacts on a body cavity and the like can be reduced. Such materials include, for example, resin materials such as polyurethane and polyurethane elastomer; and the like.

As a method of joining the front end tip 41 with the mesh member 31, the following and the like may be used: for example, a method involving embedding each front end portion of each wire 31a of the mesh member into the base end portion of the front end tip 41 by fusion and the like.

The core wire 51 serves to expand and contract the mesh member 31, and, for example, has a front end connected to the front end of the mesh member 31 and/or the front end tip 41, and extends through the space inside the mesh member 31, the lumen 21a of the second hollow shaft 21, and the lumen 11a of the first hollow shaft 11 so that a base end of the core wire 51 is located in the base end side relative to the base end of the first hollow shaft 11. The above core wire 51 has a front end side small-diameter portion 511, and a large-diameter portion 512 having an outer diameter larger than that of the front end side small-diameter portion 511 and located in the base end side relative to the front end side small-diameter portion 511. At least a portion of the large-diameter portion 512 is located in the lumen 21a of the second hollow shaft 21 in a state where the mesh member 31 remains contracted radially.

Specifically, the core wire 51, for example, has a front end joined (fixed) to the front end of the mesh member 31 and the front end tip 41, and the large-diameter portion 512 can be arranged to extend from the base end of the second hollow shaft 21 through the front end of the second hollow shaft 21 in the long axis direction in a state where the mesh member 31 remains contracted radially.

Figure 2A:
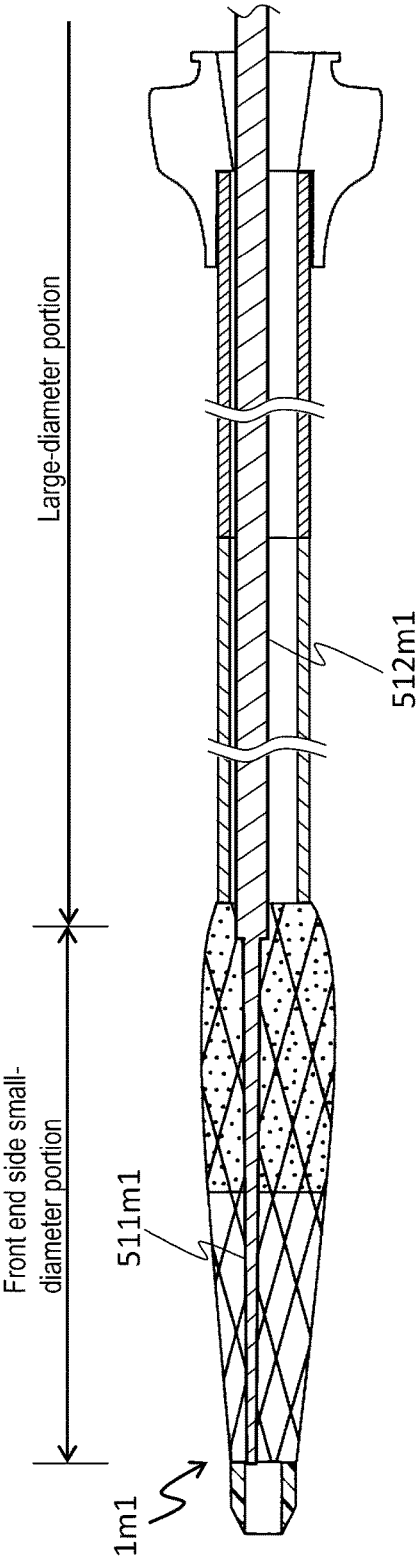
FIGS. 2A, 2B, and 2C show schematic cross-sectional views of various aspects of the front end side small-diameter portion of the core wire of FIG. 1.
Figure 2B:
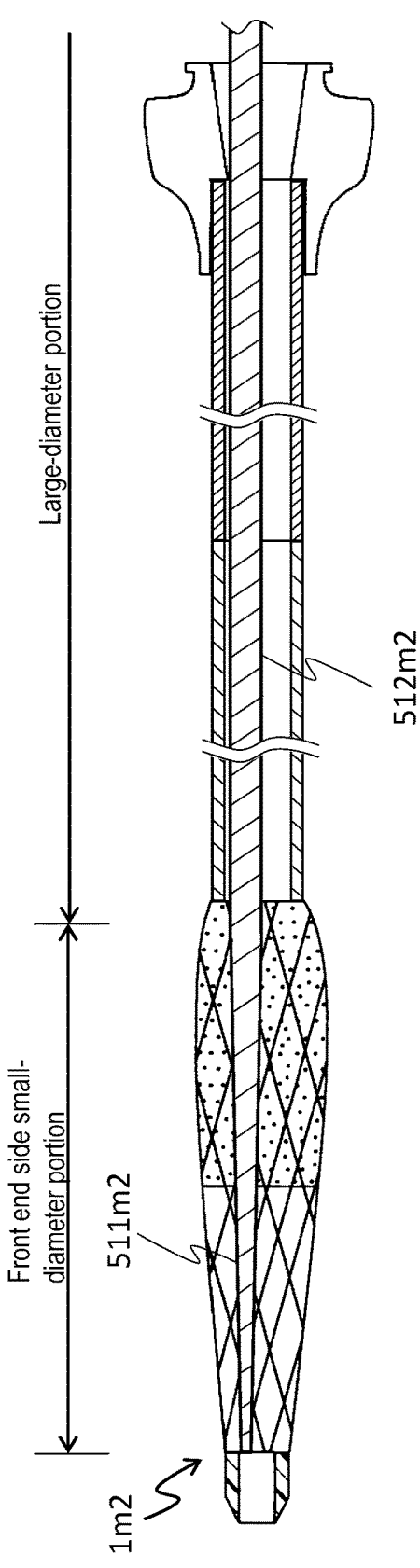
Figure 2C:
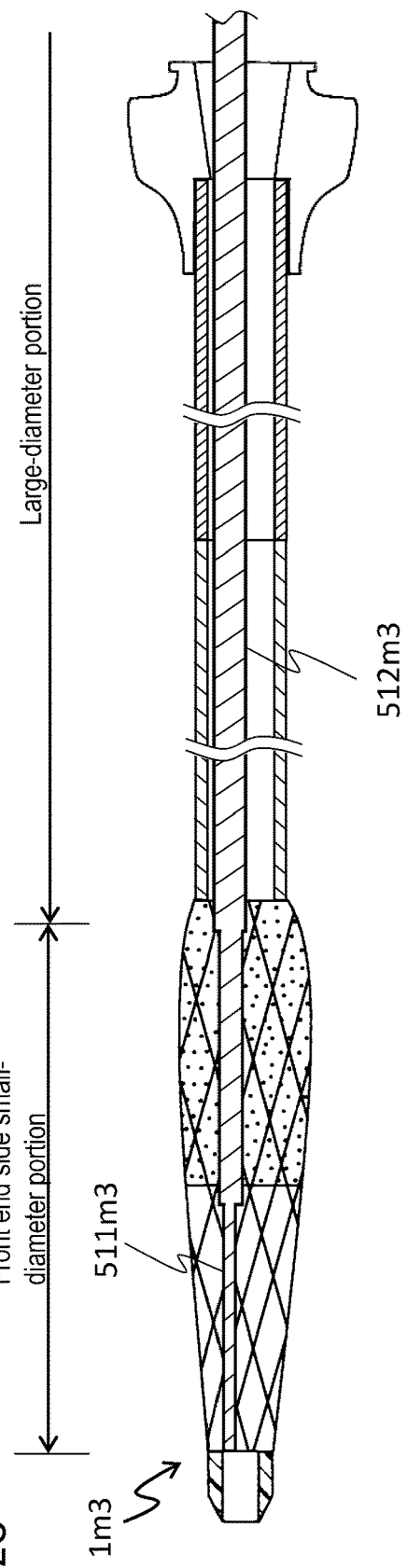

Here, the outer diameter of the front end of the front end side small-diameter portion 511 in the core wire 51 is preferably smaller than that of the base end of the front end side small-diameter portion 511. As a catheter having a shape of the front end side small-diameter portion 511 as described above, the following may be used: for example, a catheter 1m1 having a front end side small-diameter portion 511*m*1 and a large-diameter portion 512*m*1, the front end side small-diameter portion 511*m*1 having a diameter gradually decreasing toward a front end from a base end, the base end having an outer diameter being smaller than that of a front end of the large-diameter portion 512*m*1 (see FIG. 2A); a catheter 1*m*2 having a front end side small-diameter portion 511*m*2 and a large-diameter portion 512*m*2, the front end side small-diameter portion 511*m*2 having a diameter gradually decreasing toward a front end from a base end, the base end having a shape being coincide with that of a front end of the large-diameter portion 512*m*2 (see FIG. 2B); a catheter 1*m*3 having a front end side small-diameter portion 511*m*3 and a large-diameter portion 512*m*3, the front end side small-diameter portion 511*m*3 having a diameter decreasing in a step-wise fashion toward a front end from a base end (see FIG. 2C); and a catheter having a front end side small-diameter portion and a large-diameter portion, the front end side small-diameter portion having a combination of a portion having a gradually decreasing diameter and a portion having stepwisely decreasing diameter (not shown); and the like.

As described above, the outer diameters of the front ends of the front end side small-diameter portions 511*m*1 to 511*m*3 are smaller than those of the base ends of the front end side small-diameter portions 511*m*1 to 511*m*3, respectively. This can reduce stiffness even in the front end side small-diameter portions 511*m*1 to 511*m*3, increasing the flexibility of the front ends of the front end side small-diameter portions 511*m*1 to 511*m*3.

The outer diameter of the core wire 51 is, for example, 0.10 mm to 0.50 mm at the front end side small-diameter portion 511 and 0.20 mm to 0.60 mm at the large-diameter portion 512, and preferably 0.15 mm to 0.25 mm at the front end side small-diameter portion 511 and 0.30 mm to 0.40 mm at the large-diameter portion 512. It is noted that the dimension of the core wire 51 in the long axis dimension can be appropriately selected depending on the dimensions of the first and second hollow shafts 11 and 21 and the mesh member 31.

A material for the core wire 51 preferably has sufficient stiffness and tensile strength in view of ensuring reliable expansion and contraction of the mesh member 31 and preventing breakage of the core wire 51 itself. Such materials include, for example, metal materials such as stainless steel such as SUS304, nickel-titanium alloy, cobalt-chromium alloy; and the like.

As a method of joining the core wire 51 with the front end tip 41 and/or the mesh member 31, the following may be used: for example, a method involving embedding the front end portion of the core wire 51 into the base end portion of the front end tip 41 by fusion and the like, and/or a method involving welding the front end portion of the core wire 51 with the front end portion of the mesh member 51, and the like.

The core wire 51 according to the present embodiment includes the front end side small-diameter portion 511 and the large-diameter portion 512, in which a portion of the large-diameter portion 512 is arranged to extend throughout the lumen 21*a* of the second hollow shaft 21 in the long axis direction, and the large-diameter portion 512 is arranged to extend through the first hollow shaft 11 so that the base end of the large-diameter portion 512 is exposed to the outside of the connector 61 described below. Further, in the core wire 51, the front end of the front end side small-diameter portion 511 is joined to the base end portion of the front end tip 41 in the interior of the mesh member 31 by fusion and the like.

The connector 61 serves as a member with which an operator holds the catheter 1. The connector 61 is connected to the base end portion of the first hollow shaft 11, and has a lumen 61*a* and an opening 61*b*, the lumen 61*a* being in communication with the lumen 11*a* of the first hollow shaft 11 so that the base end of the core wire 51 is exposed to the outside, the opening 61*b* being formed at the base end of the lumen 61*a*. It is noted that there is no particular limitation for the form of the connector 61 as long as the effects of the present disclosure are not impaired.

The guiding film 71 is a film-shaped member having a base end located at the base end of the mesh member 31, and covering a portion of the mesh member 31. The above guiding film 71 can smoothly direct the retrograde guide wire W received through the mesh opening 31*b* of the mesh member 31 toward an opening 21*b* of the second hollow shaft 21. Specifically, the guiding film 71, for example, has a front end located between the base end of the front end tip 41 and the front end of the second hollow shaft 21, and a base end located at the front end of the second hollow shaft 21.

Materials which can be used for the guiding film 71 include, for example, polyethylene, polyurethane, polyamide, polyamide elastomer, polyolefin, polyester, polyester elastomer, and the like. Among these, polyurethane is preferably used as the above material in view of improving surface slidability.

A portion of the guiding film 71 may be joined to the mesh member 31. For example, a front end portion (for example, a front end outer periphery of the guiding film 71, and the like), a base end portion, and/or a middle portion of the guiding film 71 can be joined. As a method of joining the guiding film 71 with the mesh member 31, the following may be used: for example, a method involving heating and melting a material of the guiding film 71, and immersing the mesh member 31 into this molten material to cross-link between the wires 31*a* (occluding the mesh opening 31*b*); a method involving fusing an end of a funnel-shaped film opening and joining the above end with the mesh member 31; and the like.

The guiding film 71 according to the present embodiment has a front end located at a substantially middle portion in the long axis direction of the mesh member 31, and a base end located at the front end of the second hollow shaft 21, and is arranged so that the wires 31*a* of the mesh member 31 are cross-linked together (the mesh opening 31*b* is occluded).

Next, an operating mode of the catheter 1 will be described. It is noted that a procedure for passing the retrograde guide wire W to a site in a blood vessel where a blockage is present (hereinafter, may also be referred to "occlusion site") will be described in this section.

First, an antegrade guide wire (not shown) is inserted into a blood vessel, and then pushed to an occlusion site along the blood vessel. After the front end of the antegrade guide wire reaches the occlusion site, a balloon catheter (not shown) is inserted into the occlusion site using the antegrade guide wire as a guide. Then the balloon is inflated radially to expand the occlusion site. After the occlusion site is expanded, the balloon is deflated radially. The balloon catheter is then withdrawn out of the blood vessel.

Next, the antegrade guide wire is inserted into the catheter 1 so that the base end of the antegrade guide wire exits the opening 61*b* to the outside of the catheter 1 through a front end opening of the front end tip 41, the lumen 41*a*, the space inside the mesh member 31, the lumen 21*a*, the lumen 11*a*, and then the lumen 61*a*. The front end of the catheter 1 is then pushed to the occlusion site in the blood vessel using the antegrade guide wire as a guide. At that time, the catheter 1 in a state where the mesh member 31 remains contracted radially is inserted into the blood vessel, and the above contracted state is maintained until the front end of the catheter 1 reaches the occlusion site.

Figure 3:
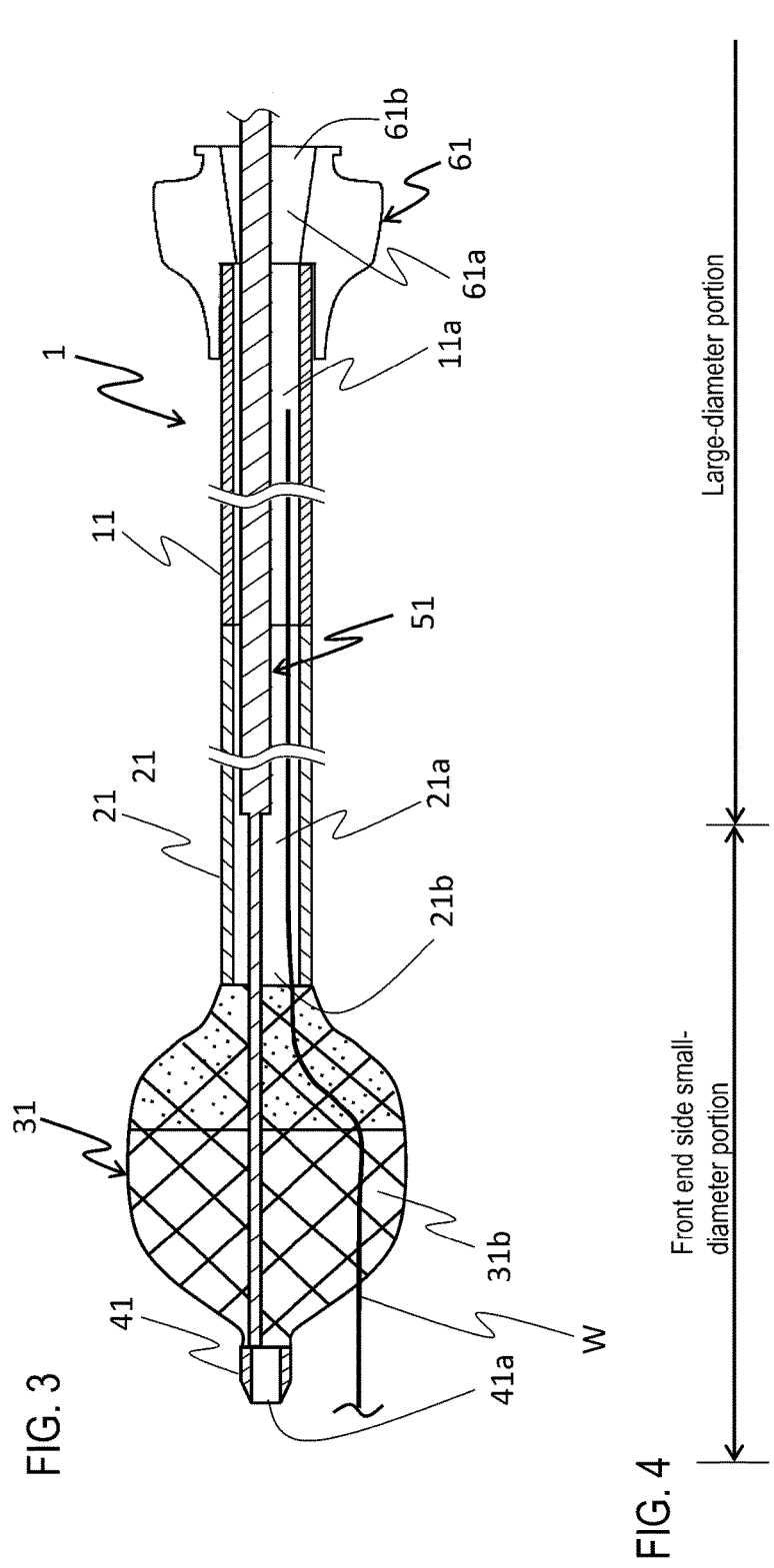
FIG. 3 shows a schematic cross-sectional view for illustrating an operating mode of FIG. 1.

Next, after the front end of the catheter 1 reaches the occlusion site expanded with the balloon catheter, the antegrade guide wire is pulled out of the catheter 1 by pulling the antegrade guide wire to the base end side of the catheter 1. Subsequently, a gap between the front end of the mesh member 31 and the front end of the second hollow shaft 21 becomes narrow by pulling the core wire 51 exposed outside through the opening 61b of the connector 61 toward the base end side. As a result of this, the mesh member 31 undergoes deformation (inflation) outwardly in the radial direction as shown in FIG. 3. Now, the mesh opening 31b is also expanded as the mesh member 31 is radially expanded, leading to a condition where the retrograde guide wire W can easily be received. In the present embodiment, the front end portion of the guiding film 71 is also radially expanded as the mesh member 31 is radially expanded, transforming the guiding film 71 into an overall funnel-like shape because the front end of the guiding film 71 is joined to the substantially middle portion of the mesh member 31 in the long axis direction. It is noted that after the front end of the catheter 1 advances along the antegrade guide wire, and reaches an occlusion site, the mesh member 31 may be radially expanded, and then the antegrade guide wire may be pulled out of the catheter 1.

Next, the retrograde guide wire W approaching from the front end side is received in the catheter 1. An approaching route of the retrograde guide wire W may likely be, for example, via a false lumen within a blood vessel wall surrounding an occlusion site, a through-hole penetrating an occlusion site, or the like, but the retrograde guide wire W can approach via any route. The retrograde guide wire W is received in the space inside the mesh member 31 through the mesh opening 31b of the mesh member 31 expanded radially, and then received in the lumen 21a of the second hollow shaft 21 through the opening 21b of the front end of the second hollow shaft 21, and further sent to the lumen 11a of the first hollow shaft 11 and the lumen 61a of the connector 61, and exits the opening 61b to the outside (the outside of the body). This can lead to a state where the retrograde guide wire W passes through the occlusion site, and the both ends of the retrograde guide wire W are exposed to the outside of the body.

In the catheter 1 as described above, the outer diameter of the large-diameter portion 512 is larger than that of the front end side small-diameter portion 511. This configuration enables the large-diameter portion 512 to reinforce the second hollow shaft 21, preventing excessive bending of the second hollow shaft 21 which is made of a resin. Consequently, this can prevent the occurrence of a kink in the second hollow shaft 21.

Further, in the catheter 1, the large-diameter portion 512 is arranged to extend from the base end of the second hollow shaft 21 through the front end of the second hollow shaft 21 in the long axis direction. This configuration can prevent excessive bending of the second hollow shaft 21 throughout in the long axis direction, further preventing the occurrence of a kink.

Figure 4:
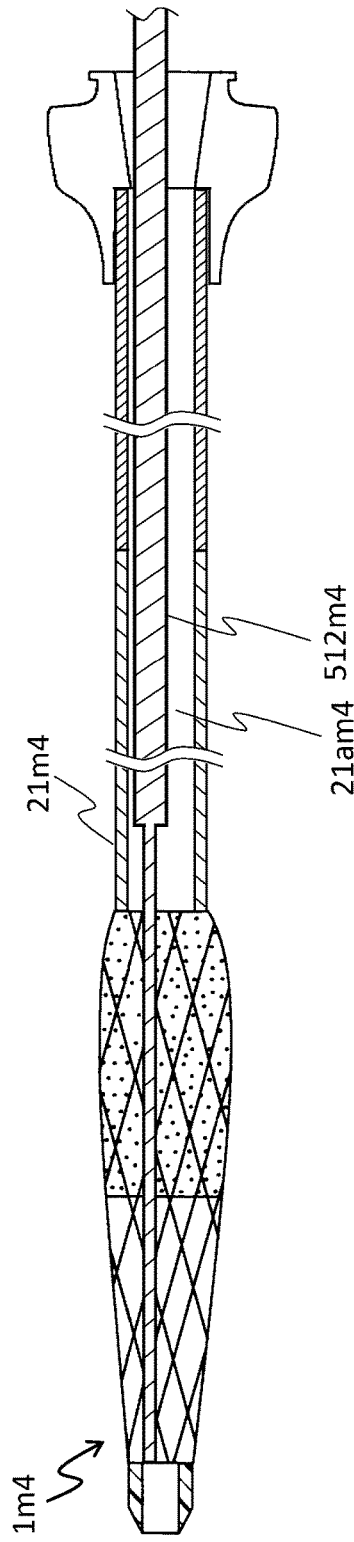
FIG. 4 shows a schematic cross-sectional view of a variation of the first embodiment.

It is sufficient that the catheter 1 has the large-diameter portion 512 arranged in at least portion of the lumen 21a of the second hollow shaft 21 in the long axis direction. For example, the catheter may be a catheter 1m4 in which the front end of the large-diameter portion 512m4 is located in the halfway of the lumen 21am4 of the second hollow shaft 21m4 in the long axis direction (see FIG. 4).

Second Embodiment

FIG. 5 shows a schematic cross-sectional view of the second embodiment. As shown in FIG. 5, a catheter 2 generally includes: a first hollow shaft 11, a second hollow shaft 21, a mesh member 31, a front end tip 41, a core wire 52, a connector 61, and a guiding film 71. The catheter 2 differs from the first embodiment in that the catheter 2 includes the core wire 52. It is noted that the catheter 2 is similar to the first embodiment except for the configuration of the core wire 52. Therefore, the same reference numerals are given to the same portions, and detailed description thereof will be omitted.

The core wire 52 has a front end connected to the front end of the mesh member 31 and/or the front end tip 41, and extends through the space inside the mesh member 31, a lumen of the second hollow shaft 21, and a lumen of the first hollow shaft 11 so that a base end is located in the base end side relative to the base end of the first hollow shaft 11. The core wire 52 has a front end side small-diameter portion 521, a large-diameter portion 522, and a base end side small-diameter portion 523, the large-diameter portion 522 having an outer diameter larger than that of the front end side small-diameter portion 521 and located in the base end side relative to the front end side small-diameter portion 521, the base end side small-diameter portion 523 having an outer diameter smaller than that of the large-diameter portion 522 and located in the base end side relative to the large-diameter portion 522, in which at least a portion of the large-diameter portion 522 is located in the lumen 21a of the second hollow shaft 21 in a state where the mesh member 31 remains contracted radially.

Specifically, in the core wire 52, for example, the front end side small-diameter portion 521, the large-diameter portion 522, and the base end side small-diameter portion 523 are provided in this order from the front end toward the base end side, and the entire of the large-diameter portion 522 may be located at a portion of the lumen 21a of the second hollow shaft in the long axis direction, and the base end side small-diameter portion 523 may be arranged so as to extend through the first hollow shaft 11 with the base end of the base end side small-diameter portion 523 exposed to the outside of the connector 61.

The outer diameter of the core wire 52 is, for example, 0.10 mm to 0.50 mm at the front end side small-diameter portion 521, 0.20 mm to 0.60 mm at the large-diameter portions 522, and 0.10 mm to 0.50 mm at the base end side small-diameter portions 523, and preferably 0.15 mm to 0.25 mm at the front end side small-diameter portion 521, 0.30 mm to 0.40 mm at the large-diameter portions 522, and 0.25 mm to 0.35 mm at the base end side small-diameter portions 523.

In the catheter 2 as described above, the outer diameter of the base end side small-diameter portion 523 is smaller than that of the large-diameter portion 522. This configuration, for example, can reduce the pressure loss of a fluid in the inside of a lumen to allow smooth injection of the fluid when the fluid is injected from the base end of the first hollow shaft 11 to flush the catheter 2.

It is sufficient that the core wire 52 of the catheter 2 has the base end side small-diameter portion 523 and the large-diameter portion 522, at least a portion of the large-diameter portion 522 being located in the lumen 21a of the second hollow shaft 21. The catheter 2 may be, for example, a catheter 2m1 in which a portion of a large-diameter portion 522m1 is located in the entire of the lumen 21a of the second hollow shaft 21 in the long axis direction (see, FIG. 6A), a catheter 2m2 in which a portion of a large-diameter portion 522m2 is located in a portion of the lumen 21a of the second hollow shaft 21 in the long axis direction (see, FIG. 6B), or a catheter 2m3 in which the entire of a large-diameter portion 522m3 is located in the entire of the lumen 21a of the second hollow shaft 21 in the long axis direction (see, FIG. 6C).

Third Embodiment

Figure 7:
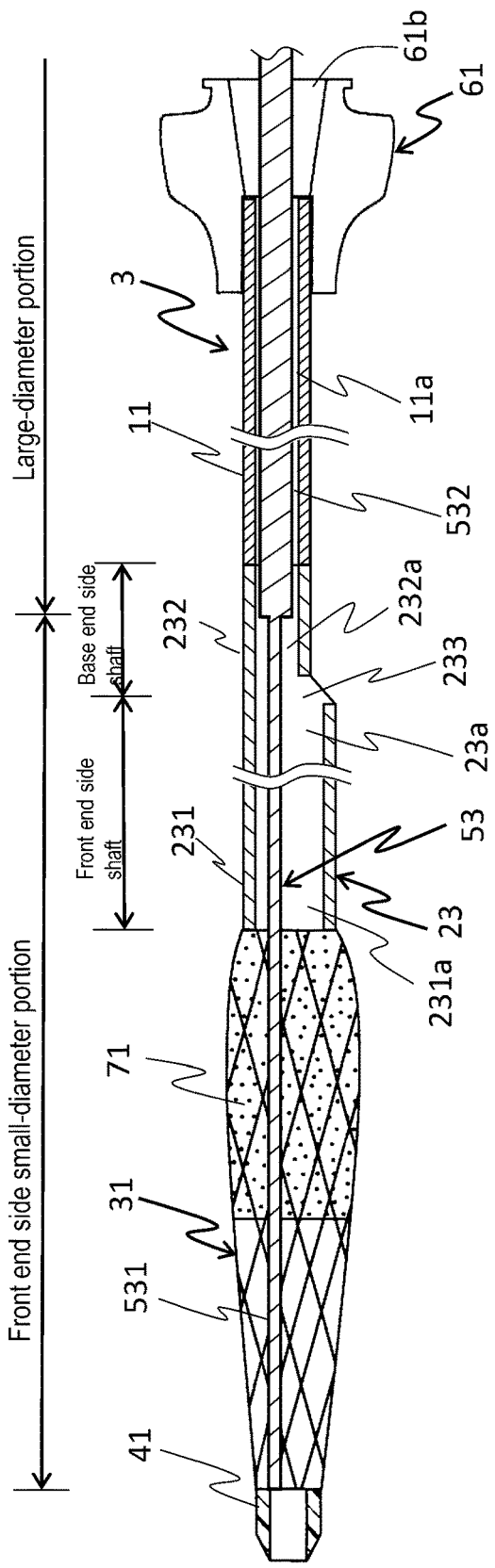
FIG. 7 shows a schematic cross-sectional view of a third embodiment.

FIG. 7 shows a schematic cross-sectional view of the third embodiment. As shown in FIG. 7, a catheter 3 generally includes: a first hollow shaft 11, a second hollow shaft 23, a mesh member 31, a front end tip 41, a core wire 53, a connector 61, and a guiding film 71. The catheter 3 differs from the first embodiment in that the catheter 3 includes the second hollow shaft 23 and the core wire 53. It is noted that the catheter 3 is similar to the catheter from the first embodiment except for the configurations of the second hollow shaft 23 and the core wire 53. Therefore, the same reference numerals are given to the same portions, and detailed description thereof will be omitted.

The second hollow shaft 23 has a communication pore 233 communicating a lumen 23a of the second hollow shaft 23 with the outside of the catheter 3 between the front end of the second hollow shaft 23 and the base end of the second hollow shaft 23 in the long axis direction of the second hollow shaft 23.

Specifically, the second hollow shaft 23, for example, includes a front end side shaft 231 joined (fixed) to the base end of the mesh member 31 and a base end side shaft 232 connected to the base end of the front end side shaft 231, in which the communication pore 233 (an opening in the base end of the front end side shaft 231) may be configured to open toward the base end side at the boundary portion between the front end side shaft 231 and the base end side shaft 232.

The core wire 53 has a front end connected to the front end of the mesh member 31 and/or the front end tip 41, and extends through the space inside the mesh member 31, a lumen of the second hollow shaft 23, and a lumen of the first hollow shaft 11 so that a base end is located in the base end side relative to the base end of the first hollow shaft 11. The core wire 53 has a front end side small-diameter portion 531 and a large-diameter portion 532, the large-diameter portion 532 having an outer diameter larger than that of the front end side small-diameter portion 531 and being located in the base end side relative to the front end side small-diameter portion 531, in which at least a portion of the large-diameter portion 532 is located in the lumen 23a of the second hollow shaft 23.

Specifically, in the core wire 53, the front end side small-diameter portion 531 and the large-diameter portion 532, for example, are provided in this order from the front end toward the base end side, and the front end of the large-diameter portion 532 (the base end of the front end side small-diameter portion 531) may be arranged so as to be located between the base end of the communication pore 233, and the base end of the base end side shaft 232. Further, the core wire 53 is inserted through into a lumen 231a of the front end side shaft 231, a lumen 232a of the base end side shaft 232, and the lumen 11a of the first hollow shaft 11, and has a base end delivered to the outside through the opening 61b of the connector 61.

Figure 8A:
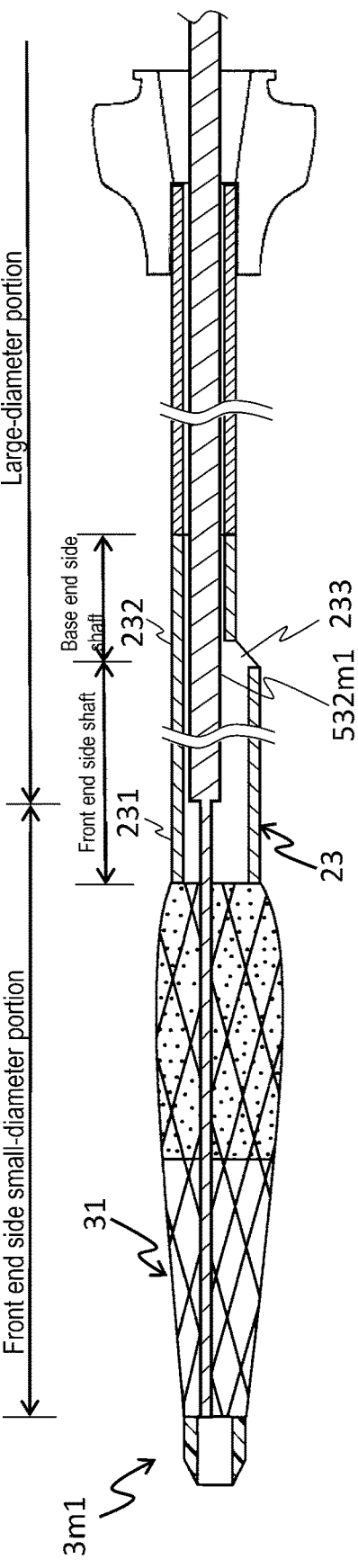

Here, the large-diameter portion 532 of the core wire 53 is preferably arranged from at least the base end of the communication pore 233 through the base end of the second hollow shaft 23 in the long axis direction in a state where the mesh member 31 remains contracted radially. As a catheter including such a core wire, the following may be used: for example, a catheter 3m1 in which the front end of the large-diameter portion 532m1 is located inside the front end side shaft 231 (see FIG. 8A), a catheter 3m2 in which the front end of the large-diameter portion 532m2 is located between the base end of the front end tip 41 and the front end of the front end side shaft 231 (see FIG. 8B), and the like.

As described above, the large-diameter portions 532m1, 532m2 are each arranged form at least the base end of the communication pore 233 through the base end of the second hollow shaft 23 in the long axis direction in a state where the mesh member 31 remains contracted radially. When an antegrade guide wire is used, for example, the configurations of these catheters can prevent excessive bending of a portion of the base end side shaft 232 of the second hollow shaft 23 made of a resin, through which the antegrade guide does not extend. Consequently, this can prevent the occurrence of a kink in the base end side shaft 232.

Further, as shown in FIG. 8C, the front end side small-diameter portion 531m3 is preferably arranged to extend from at least the front end of the communication pore 233 through the front end of the second hollow shaft 23 in the long axis direction in a state where the mesh member 31 remains contracted radially. That is, the base end of the front end side small-diameter portion 531m3 (the front end of the large-diameter portion 532m3) is preferably located between the front end and the base end of the communication pore 233, and the core wire within the lumen 231a of the front end side shaft 231 is entirely configured to be the front end side small-diameter portion 531m3.

As described above, the front end side small-diameter portion 531m3 is arranged to extend from the front end of the communication pore 233 through the front end of the second hollow shaft 23 in a state where the mesh member 31 remains contracted radially. This configuration, for example, can secure a wider passage space for an antegrade guide wire and a retrograde guide wire inserted between a front end opening 23b of the second hollow shaft 23 and the communication pore 233 in the lumen 23a of the second hollow shaft 23, enabling smooth through-insertion of these guide wires.

In the catheter 3 as described above, the outer diameter of the large-diameter portion 532 is larger than that of the front end side small-diameter portion 531. This configuration enables the large-diameter portion 532 to reinforce the second hollow shaft 23, preventing excessive bending of the second hollow shaft 23 made of a resin. Consequently, this can prevent the occurrence of a kink in the second hollow shaft 23.

Fourth Embodiment

Figure 9:
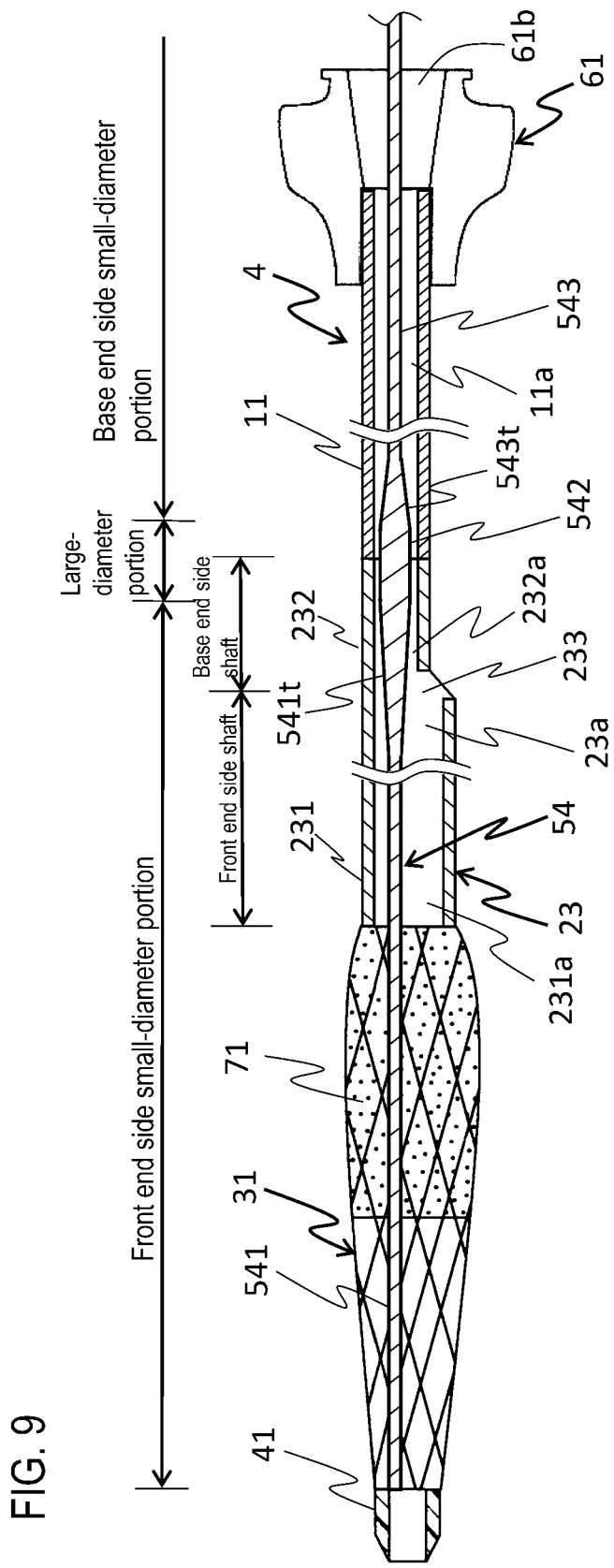
FIG. 9 shows a schematic cross-sectional view of a fourth embodiment.

FIG. 9 shows a schematic cross-sectional view of the fourth embodiment. As shown in FIG. 9, a catheter 4 generally includes: a first hollow shaft 11, a second hollow shaft 23, a mesh member 31, a front end tip 41, a core wire 54, a connector 61, and a guiding film 71. The catheter 4 differs from the third embodiment in that the catheter 4 includes the core wire 54. It is noted that the catheter 4 is similar to the catheter from the third embodiment except for the configuration of the core wire 54. Therefore, the same reference numerals are given to the same portions, and detail description thereof will be omitted.

The core wire 54 has a front end connected to the front end of the mesh member 31 and/or the front end tip 41, and extends through the space inside the mesh member 31, a lumen of the second hollow shaft 23, and a lumen of the first hollow shaft 11 so that a base end is located in the base end side relative to the base end of the first hollow shaft 11. The core wire 54 has a front end side small-diameter portion 541, a large-diameter portion 542, and a base end side small-diameter portion 543, the large-diameter portion 542 having an outer diameter larger than that of the front end side small-diameter portion 541 and located in the base end side relative to the front end side small-diameter portion 541, the base end side small-diameter portion 543 having an outer diameter smaller than that of the large-diameter portion 542 and located in the base end side relative to the large-diameter portion 542, in which at least a portion of the large-diameter portion 542 is located in the lumen 23a of the second hollow shaft 23 in a state where the mesh member 31 remains contracted radially.

Specifically, in the core wire 54, the front end side small-diameter portion 541, the large-diameter portion 542, and the base end side small-diameter portion 543, for example, are provided in this order from the front end toward the base end side, and a portion of the large-diameter portion 542 may be located at a portion of the lumen 23a of the second hollow shaft 23 in the long axis direction, and the base end side small-diameter portion 543 may be arranged so as to extend through the first hollow shaft 11 with the base end of the base end side small-diameter portion 543 exposed to the outside of the connector 61.

Here, the core wire may have a tapered portion with a diameter increasing gradually or stepwisely toward the large-diameter portion at a region in the side of the large-diameter portion in the front end side small-diameter portion and/or the base end side small-diameter portion. With regard to such a tapered portion, for example, the catheter 4 according to the present embodiment may be exemplified which has a tapered portion 541t at a region in the base end side of the front end side small-diameter portion 541 and a tapered portion 543t in the front end side of the base end side small-diameter portion 543.

For example, the tapered portions 541t, 543t provided in the core wire 54 as described above can gradually enhance the flexibility of the core wire 54 in the front end side small-diameter portion 541 toward the front end, allowing smooth injection of a flushing fluid, and the like at the base end side small-diameter portion 543.

It is noted that the outer diameter of the core wire 54 may be similar to, for example, that of the second embodiment. Further, the dimensions of the tapered portions 541t, 543t in the long axis direction can be appropriately selected depending on, for example, the positions of the front end and the base end of the large-diameter portion 542, and the like.

In the catheter 4 as described above, the outer diameter of the large-diameter portion 542 is larger than that of the front end side small-diameter portion 541. This configuration enables the large-diameter portion 542 to reinforce the second hollow shaft 23, preventing excessive bending of the second hollow shaft 23 made of a resin. Consequently, this can prevent the occurrence of a kink in the second hollow shaft 23.

It is sufficient that the catheter 4 has the communication pore 233, and the core wire 54 has the front end side small-diameter portion 541, the large-diameter portion 542, and the base end side small-diameter portion 543, at least a portion of the large-diameter portion 542 being located in the lumen 23a of the second hollow shaft 23. As the catheter 4, the following may be used: for example, a catheter 4m1 including a front end side small-diameter portion 541m1 having a tapered portion 541tm1 and a base end side small-diameter portion 543m1 having a tapered portion 543tm1, in which the front end of the large-diameter portion 542m1 is located in the inside of a front end side shaft 231 (see FIG. 10A); a catheter 4m2 including a front end side small-diameter portion 541m2 having a tapered portion 541tm2 and a base end side small-diameter portion 543m2 having a tapered portion 543tm2, in which the front end of the large-diameter portion 542m2 is located between the base end of a front end tip 41 and the front end of a front end side shaft 231 (see FIG. 10B); a catheter 4m3 including a front end side small-diameter portion 541m3 having a tapered portion 541tm3 and a base end side small-diameter portion 543m3 having a tapered portion 543tm3, in which the front end of the large-diameter portion 542m3 is located between the front end and base end of a communication pore 233 (see FIG. 10C); a catheter 4m4 including a core wire 54m4 having no tapered portion, in which the entire of a large-diameter portions 542m4 is located at a portion of a lumen 23a of a second hollow shaft 23 in the long axis direction (see FIG. 10D); and the like.

Figure 10C:
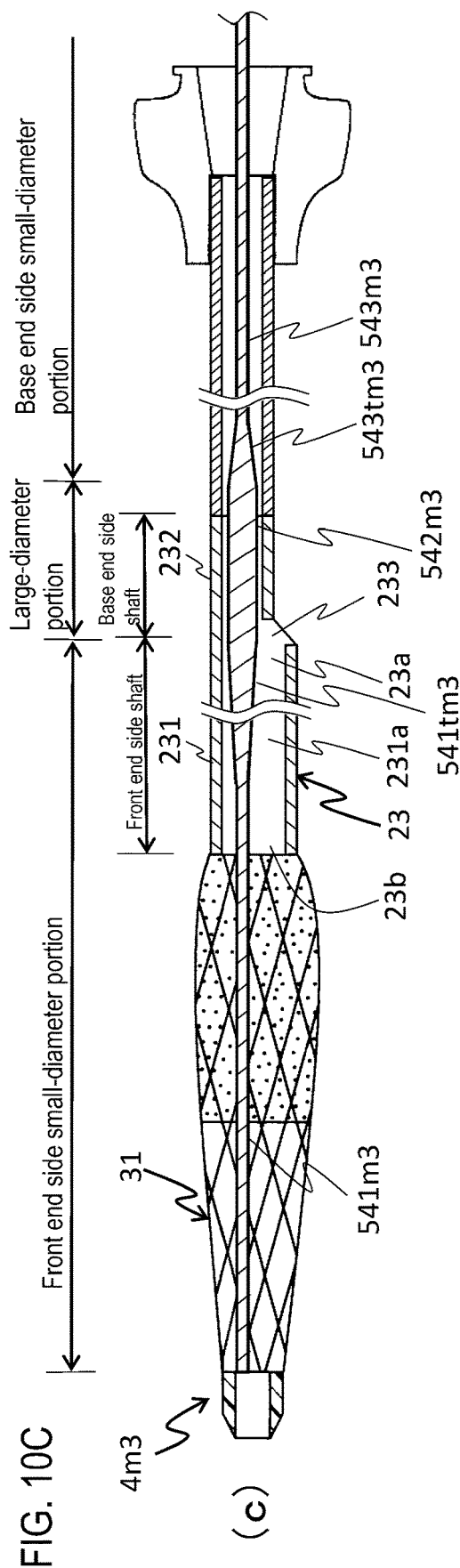

It is noted that the catheter 4m3 of FIG. 10C is preferably configured so that the base end of the large-diameter portion 542m3 is located near the boundary between a base end side shaft 232 of a second hollow shaft 23 and a first hollow shaft 11.

Figure 10D:
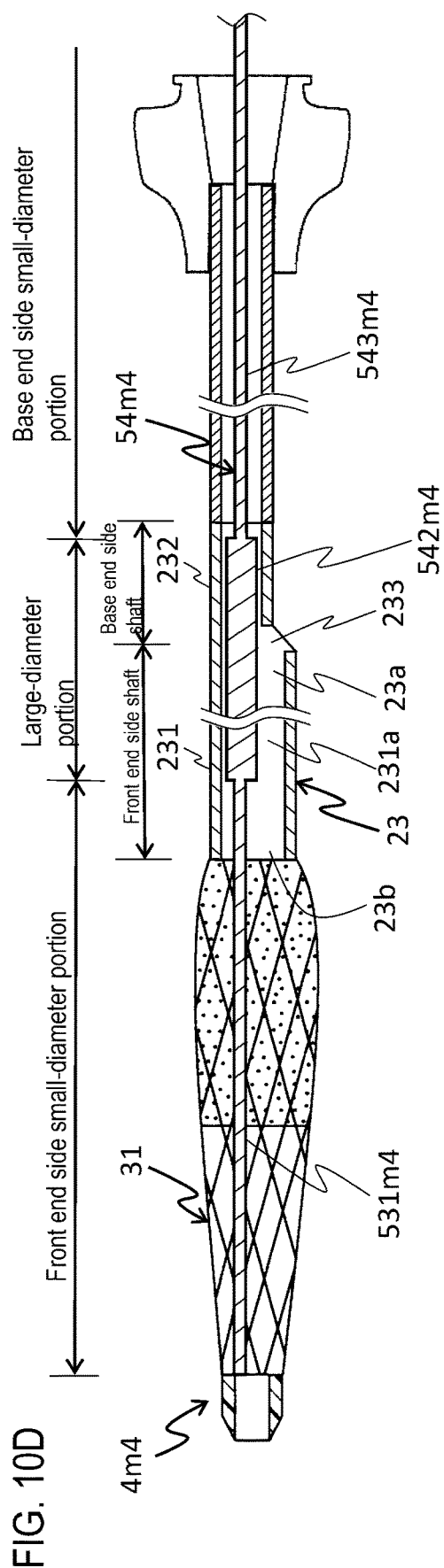

The catheter 4m4 of FIG. 10D is preferably configured so that the front end of the large-diameter portion 542m4 is located between the front end and base end of a communication pore 233, and the base end of the large-diameter portion 542m4 is located near the boundary of a base end side shaft 232 of the second hollow shaft 23 and a first hollow shaft 11.

It is noted that the present disclosure shall not be limited to the configurations of the aforementioned embodiments. All of alternations made within the scope of the claims and within the meaning and range equivalent to the scope of the claims are intended to be included.

For example, the catheters 1 to 4 each including the connector 61 and the guiding film 71 are described in the aforementioned embodiments, but a catheter including neither the connector nor the guiding film or a catheter including only one of the connector or the guiding film may be used.

Moreover, the catheter 4 including the core wire 54 having the tapered portions 541t, 543t is described above in the fourth embodiment, but a catheter may be used including a core wire having a tapered portion at neither the front end side small-diameter portion nor the base end side small-diameter portion, or a catheter including a core wire having a tapered portion in only one of the front end side small-diameter portion or the base end side small-diameter portion.

The invention claimed is:
1. A catheter comprising:
a first hollow shaft made of a first material;
a second hollow shaft made of a second material, and connected to a front end of the first hollow shaft;

a mesh member with a tubular shape, the mesh member being connected to a front end of the second hollow shaft and configured to expand and contract in a radial direction;

a front end tip connected to a front end of the mesh member; and a core wire having a front end connected to the front end of the mesh member and/or connected to the front end tip, the core wire extending inside the mesh member, inside a lumen of the second hollow shaft, and inside a lumen of the first hollow shaft so that a base end of the core wire is located on a base end side of the catheter relative to a base end of the first hollow shaft, wherein the core wire has a front end side small-diameter portion, a large-diameter portion having an outer diameter larger than an outer diameter of the front end side small-diameter portion and located on a base end side of the front end side small-diameter portion, and a base end side small-diameter portion having an outer diameter smaller than the outer diameter of the large-diameter portion and located on a base end side of the large-diameter portion, and at least a portion of the large-diameter portion is located in the lumen of the second hollow shaft in a state where the mesh member remains radially contracted.

2. The catheter according to claim 1, wherein
the second hollow shaft has a communication pore communicating between the lumen of the second hollow shaft and an outside of the catheter, the communication pore being located between the front end of the second hollow shaft and a base end of the second hollow shaft in a long axis direction of the second hollow shaft, and the large-diameter portion is arranged to extend from at least a base end of the communication pore through the base end of the second hollow shaft in the long axis direction in the state where the mesh member remains radially contracted.

3. The catheter according to claim 2, wherein the front end side small-diameter portion is arranged to extend from at least a front end of the communication pore through the front end of the second hollow shaft in the long axis direction in the state where the mesh member remains radially contracted.

4. The catheter according to claim 1, wherein the large-diameter portion is arranged to extend from a base end of the second hollow shaft through the front end of the second hollow shaft in a long axis direction in the state where the mesh member remains radially contracted.

5. The catheter according to claim 1, wherein an outer diameter of a front end of the front end side small-diameter portion is smaller than an outer diameter of a base end of the front end side small-diameter portion.

6. The catheter according to claim 1, wherein
the first material is metal, and
the second material is resin.

* * * * *